United States Patent
Dunn et al.

(10) Patent No.: US 6,528,080 B2
(45) Date of Patent: Mar. 4, 2003

(54) BIODEGRADABLE POLYMER COMPOSITION

(75) Inventors: Richard L Dunn, Fort Collins, CO (US); James P. English, Chelsea, AL (US)

(73) Assignee: Atrix Laboratories, Inc., Fort Collins, CO (US)

( * ) Notice: Subject to any disclaimer, the term of this patent is extended or adjusted under 35 U.S.C. 154(b) by 0 days.

(21) Appl. No.: 10/047,483

(22) Filed: Jan. 14, 2002

(65) Prior Publication Data

US 2002/0090398 A1 Jul. 11, 2002

Related U.S. Application Data

(62) Division of application No. 09/442,203, filed on Nov. 16, 1999.

(51) Int. Cl.[7] .................................................. A61F 2/00
(52) U.S. Cl. ........................................................ 424/426
(58) Field of Search ...................... 424/426, 484, 424/501, 502

(56) References Cited

U.S. PATENT DOCUMENTS

| | | | |
|---|---|---|---|
| 4,652,441 A | 3/1987 | Okada et al. ................ 424/19 |
| 4,917,893 A | 4/1990 | Okada et al. ............... 424/423 |
| 4,938,763 A | 7/1990 | Dunn et al. ............... 604/891.1 |
| 4,954,298 A | 9/1990 | Yamamoto et al. ......... 264/4.6 |
| 5,061,492 A | 10/1991 | Okada et al. .............. 424/423 |
| 5,324,519 A | 6/1994 | Dunn et al. ................. 424/426 |
| 5,330,767 A | 7/1994 | Yamamoto et al. ......... 424/497 |
| 5,447,725 A | 9/1995 | Damani et al. ............. 424/435 |
| 5,476,663 A | 12/1995 | Okada et al. ............... 424/423 |
| 5,480,656 A | 1/1996 | Okada et al. ............... 424/493 |
| 5,487,897 A | 1/1996 | Polson et al. .............. 424/426 |
| 5,538,739 A | 7/1996 | Bodmer et al. ............. 424/501 |
| 5,575,987 A | 11/1996 | Kamei et al. .............. 424/451 |
| 5,631,020 A | 5/1997 | Okada et al. ............... 424/451 |
| 5,631,021 A | 5/1997 | Okada et al. ............... 424/451 |
| 5,639,480 A | 6/1997 | Bodmer et al. ............. 424/501 |
| 5,643,607 A | 7/1997 | Okada et al. ............... 424/493 |
| 5,651,990 A | 7/1997 | Takada et al. .............. 424/497 |
| 5,688,530 A | 11/1997 | Bodmer et al. ............. 424/501 |
| 5,702,716 A | 12/1997 | Dunn et al. ................. 424/422 |
| 5,922,338 A | 7/1999 | Brich et al. ................. 424/422 |
| 5,922,682 A | 7/1999 | Brich et al. .................. 514/23 |

FOREIGN PATENT DOCUMENTS

| | | |
|---|---|---|
| GB | 2145422 | 3/1985 |
| WO | 98/44020 | 7/2001 |

*Primary Examiner*—Carlos Azpuru
(74) *Attorney, Agent, or Firm*—Schwegman, Lundberg, Woessner & Kluth, P.A.

(57) ABSTRACT

A flowable composition containing a biocompatible, biodegradable, branched thermoplastic polymer is used to form solid matrices such as implants and controlled-release, drug-compositions in a body. The flowable composition with or without bioactive agent can be administered by syringe and needle to form in situ a solid matrix. Alternatively, the flowable composition can be used to form ex vivo solid biodegradable matrices such as articles, implants and devices. The articles implants and the like can then used as solid fasteners, prosthetic devices, and controlled drug compositions.

34 Claims, 4 Drawing Sheets

BIODEGRADABLE POLYMER COMPOSITION

CROSS-REFERENCE TO RELATED APPLICATION(S)

This application is a divisional of U.S. patent application Ser. No. 09/442,203, filed on Nov. 16, 1999, now allowed, the specification of which is incorporated herein by reference.

BACKGROUND OF THE INVENTION

Biodegradable polymers have been used for many years in medical applications. Medical devices made from biodegradable polymers include sutures, surgical clips, staples, implants, and drug delivery systems. The majority of these biodegradable polymers have been solid thermoplastic materials based upon glycolide, lactide, caprolactone, and copolymers thereof. Some of these biodegradable polymers are star-branched polymers, such as those disclosed in U.S. Pat. Nos. 5,922,338 and 5,922,682, which can be used in sustained release medical devices (U.S. Pat. Nos. 5,538,739; 5,639,480; and 5,688,530).

Placing medical devices such as implants and other solid articles in a body frequently involves a surgical procedure. An incision is made, for example, and the solid implant is positioned within a body at the site of the incision. In other variants, such as disclosed in U.S. Pat. No. 4,938,763 the biodegradable polymer is introduced in a body as a flowable formulation. In these examples, a solution of the biodegradable polymer and an organic solvent is injected into a body. Upon contact with aqueous or body fluid, the polymer coagulates, forming a solid implant.

Flowable formulations often require the use of differing concentrations of polymers depending upon the particular application intended. However, typical biodegradable polymers do not function well at widely variant concentrations in flowable delivery systems.

Consequently, there is a need for a method and composition which provides a biodegradable, polymer system that functions at widely different concentrations of polymer. Specifically, there is a need for a method and composition for a pharmaceutical system that can be used to provide implants of all kinds and also to provide controlled delivery systems.

SUMMARY OF THE INVENTION

These and other needs are met by the present invention, which is directed to a flowable composition suitable for use in medical applications. The present invention is also directed to the use of branched biodegradable biocompatible thermoplastic polymers as in situ and ex vivo solid matrices, and as delivery systems. The in situ and ex vivo implants as well as the delivery systems are produced by solidification of the flowable composition through its contact with aqueous medium, body fluid or water. The ex vivo implants are formed outside the body and are used as solid devices. They include, for example, microcapsules, microparticles, single body implants, sutures, surgical clips, staples, and stents.

The flowable composition is a solution or dispersion of a branched, biocompatible, biodegradable thermoplastic polymer or copolymer that is at least substantially water-insoluble and an organic solvent that is biocompatible and is at least slightly soluble in aqueous medium, water or body fluid. Once the flowable composition is placed into a substrate such as a body or aqueous medium, the polymer coagulates or solidifies into a solid matrix. The placement of the flowable composition can be anywhere within the body, including soft tissue such as muscle or fat, hard tissue such as bone, or a cavity such as the periodontal, oral, vaginal, rectal, nasal, or a pocket such as a periodontal pocket or the cul-de-sac of the eye.

In applications in which the flowable composition is used for controlled drug release, a biologically active agent is added to the composition. The biologically active agent is dissolved or dispersed in the composition of branched, biocompatible, biodegradable thermoplastic polymer and organic solvent to form a solution, suspension or dispersion. When this pharmaceutical composition is contacted with an aqueous medium, with a body fluid or with water, a solid polymer-bioactive agent matrix is formed.

Rate modifying agents to control the rate of release of the bioactive agent relative to the solid matrix without the additive can be included. Preservatives, homogenization agents, surfactants, colorants, fillers, and excipients can also be included.

Several advantages are achieved with the flowable composition of the invention compared with other systems. The flowable composition may be injected via syringe and needle into a body while it is in flowable form and will form in situ a solid biodegradable matrix. The need to form an incision is eliminated, and the implant will assume the shape of its cavity. A drug releasing implant may be provided by adding a biologically active agent to the flowable composition system prior to injection. Once the implant is formed, it will release the bioactive agent to the body over a period of time and will also biodegrade. The so-called burst effect or initial release of bioactive agent can be controlled with the flowable composition because high concentrations of polymer can be used in the flowable composition. Further, the same bioactive agent release profile as provided by implants from linear polymer compositions is achieved.

The invention also relates to solid articles for medical applications that are formed from the flowable compositions. Solid articles such as microcapsules, microparticles, monolithic implants, fasteners, medical devices, and controlled drug release systems are produced by ex vivo solidification of the flowable composition. The solid articles are then utilized within a body by, for example, suturing, clipping, insertion, injection, incision, inhalation and the like. When used as surgical clips, sutures, and pins, the solid articles provide needed support in medical applications. When used as drug release implants, these solid articles provide the controlled release of a bioactive agent.

DETAILED DESCRIPTION OF THE INVENTION

Figure 1:
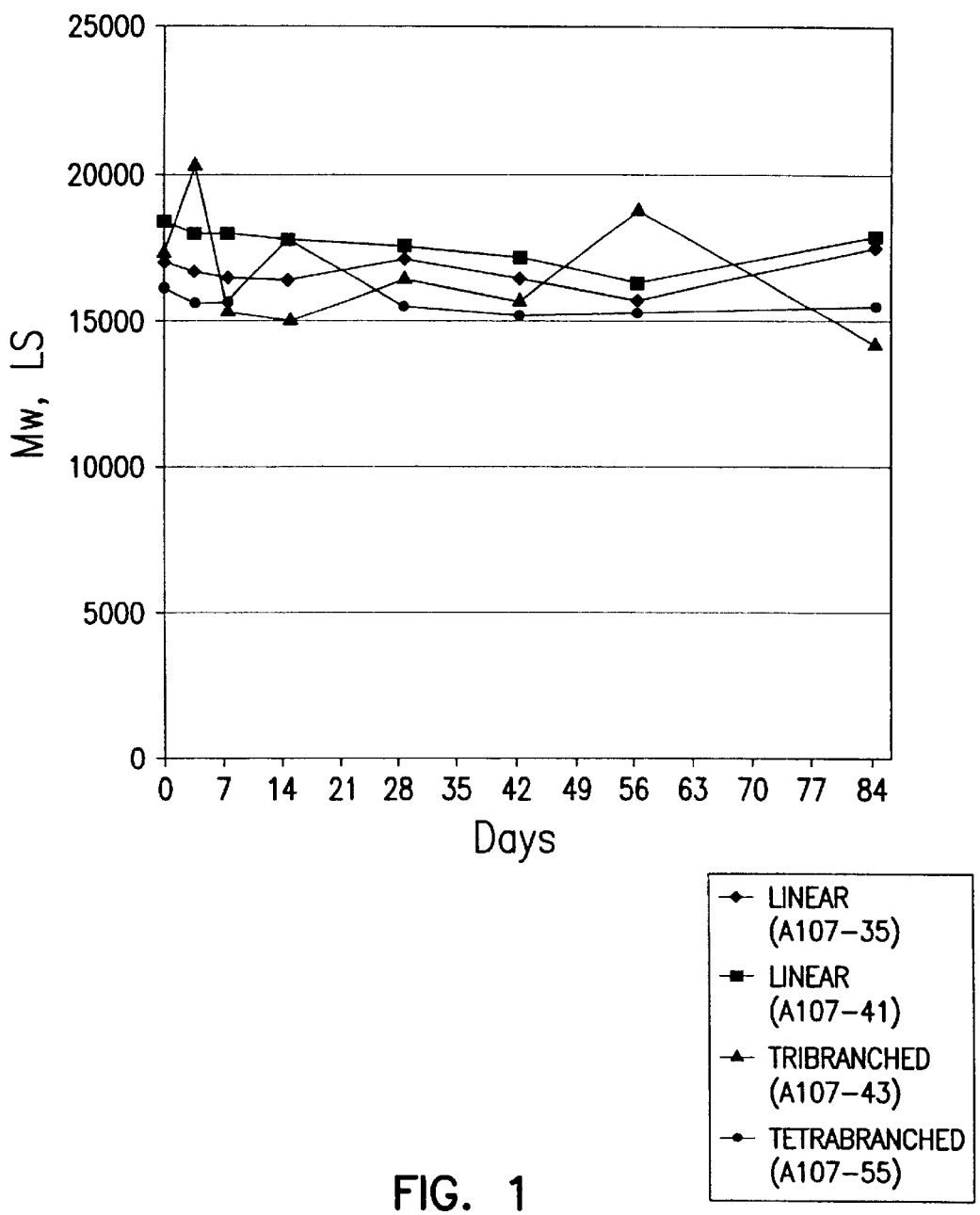
FIG. 1 shows the results of Degradation Study 1.

The present invention is directed to a flowable composition composed of a biocompatible, biodegradable, branched, thermoplastic polymer and an organic solvent. The branched thermoplastic polymer is at least substantially, preferably essentially completely soluble, in the organic solvent and is at least substantially, preferably completely insoluble in aqueous medium, body fluid and water. The organic solvent is at least slightly soluble in water, preferably moderately soluble in water, and especially preferably substantially soluble in water. The flowable composition is pharmaceutically suitable for injection into a body wherein it will form a pharmaceutically acceptable, solid matrix, which typically is a single body implant or drug delivery system. In one aspect of the flowable composition, a biologically active agent is included and the solid implant will release the biologically active agent at a controlled rate. The rate of release may be altered to be faster or slower by inclusion of a rate-modifying agent.

The present invention also is directed to biodegradable implants and methods for producing the same. These implants are solid articles that can be made from the flowable composition. Included are microcapsules, microparticles, structured articles such as sutures, staples, medical devices, stents and the like as well as monolithic implants and implant films, filamentous membranes and matrices. These implants differ in microscopic structures from known materials due to the method (i.e., coagulation) by which they are made.

The microcapsules are dimensioned on the order of 10 to 400 microns, and preferably are dimensioned so as to avoid causing emboli if introduced into the blood stream of a mammal. They are typically composed of a porous shell of the thermoplastic, branched polymer and a core of another material such as a bioactive agent or a bioactive agent in a diluent or carrier.

The microparticles have approximately the same dimensions as microcapsules. The microparticles are typically composed of a porous matrix of the thermoplastic, branched polymer and bioactive agent. The bioactive agent is typically contained within the polymer matrix as a homogeneous dispersion or solution, or as heterogeneous domains.

The structured articles have the known shapes as indicated by the information conveyed by their names. They may or may not contain bioactive agent. The monolithic implants are single body implants formed outside the body by solidification of the flowable composition in an aqueous medium. The differing shapes may be obtained by use of a molding or extrusion device designed to provide such shapes as the flowable composition is contacted with the solidification bath. These implants may have such shapes as spherical, elipsoidal, cylindrical, string-like, or disc-like as well as any other appropriate shape for placement into a body location.

The films may or may not contain bioactive agent. They may be formed by casting upon the aqueous medium or by other techniques known to provide such films.

The filamentous membranes also may or may not contain a bioactive agent. They may be formed by the technique of described in copending U.S. patent application Ser. No. 09/110723, filed Jul. 7, 1998, the disclosure of which is incorporated herein by reference.

Flowable Composition

According to the present invention, a flowable composition is provided in which a biocompatible, branched, biodegradable, thermoplastic polymer is dissolved or dispersed in a biocompatible organic solvent. Upon contact with an aqueous medium, body fluid or water, the flowable composition solidifies to form an implant or implantable article. The implants and implantable articles that are formed from the flowable polymer compositions of the present invention can be used for controlled drug release. In these applications, a bioactive agent is added to the flowable composition. The bioactive agent is contained within the solidified polymer matrix when the flowable composition undergoes its transformation to an implant or implantable article. When the implant is present within a body, the bioactive agent is released in a sustained manner through diffusion through the polymer matrix, by direct dissolution at the implant surfaces and by degradation and erosion of the thermoplastic polymer.

The use of the branched thermoplastic polymer in the flowable composition provides an ability to use a higher solids content for the flowable composition relative to flowable mixtures formed with linear thermoplastic polymers such as those described in U.S. Pat. No. 4,938,763. Typically, a high solids content, such as 50 wt % or more, of linear thermoplastic polymer of average molecular weight of 40,000 or more in a biocompatible organic solvent results in a solution viscosity so high that the mixture of linear thermoplastic polymer and organic solvent will not be readily flowable. While these mixtures are not readily flowable, they flow sufficiently to be used as puttys or thick gels for direct placement and manipulation in a surgically created or augmented site in the body. Use of a flowable composition of the present invention at high solids contents, however, results in readily flowable compositions that can be injected. At the same solids contents and polymer average molecular weights, the flowable compositions of the present invention have lower viscosities than the linear thermoplastic polymer mixtures disclosed in the '763 patent.

It is believed that a high solids content of branched thermoplastic polymer in the flowable compositions of the present invention will provide substantial control of the so-called burst effect. The burst effect is the initial release of bioactive agent from the flowable composition as it is transforming to a solid implant. It is believed to occur as a result of aqueous or body fluid infusion into the flowable composition and dispersion of the organic solvent from the flowable composition during this transformation stage. Typically, the burst effect of a transforming mixture of thermoplastic polymer, organic solvent and bioactive agent such as that described in U.S. Pat. No. 4,938,763 releases a spiked concentration of bioactive agent over a short period of time. This spiked initial release is often undesirable.

Polymer

The biocompatible, biodegradable, branched, thermoplastic polymers used according to the invention can be made from a variety of monomers which form polymer chains or monomeric units joined together by linking groups. These include polymers with polymer chains or backbones containing such linking groups as ester, amide, urethane, anhydride, carbonate, urea, esteramide, acetal, ketal, and orthocarbonate groups as well as any other organic functional group that can be hydrolyzed by enzymatic or hydrolytic reaction (i.e., is biodegradable by this hydrolytic action). These polymers are usually formed by reaction of starting monomers containing the reactant groups that will form these backbone linking groups. For example, alcohols and carboxylic acids will form ester linking groups. Isocyanates and amines or alcohols will respectively form urea or urethane linking groups.

According to the present invention, some fraction of one of these starting monomers will be at least trifunctional, and preferably multifunctional. This multifunctional character provides at least some branching of the resulting polymer chain. For example, when the polymer chosen contains ester linking groups along its polymer backbone, the starting monomers normally will either be hydroxycarboxylic acids or will be diols and dicarboxylic acids. The polymers of the present invention are obtained by inclusion of some fraction of a starting monomer that is at least multifunctional. In addition, the branched polymers of the present invention may incorporate more than one multifunctional unit per polymer molecule, and typically many multifunctional units depending on the stoichiometry of the polymerization reaction. Preferably, the branched polymers of the present invention incorporate at least one multifunctional unit per polymer molecule. A so-called star-branched polymer is formed when one multifunctional unit is incorporated in each polymer molecule.

For example, for the ester linking group polymer described above, a dihydroxycarboxylic acid would be included with the first kind of starting monomer, or a triol and/or a tricarboxylic acid would be included with the second kind of starting monomer. Similarly, a triol, quatraol, pentaol, or hexaol such as sorbitol or glucose can be included with the first kind of starting monomer. The same rationale would apply to polyamides. A triamine and/or triacid would be included with starting monomers of a diamine and dicarboxylic acid. An amino dicarboxylic acid, diamino carboxylic acid or a triamine would be included with the second kind of starting monomer, amino acid. Any aliphatic, aromatic or arylalkyl starting monomer having the specified functional groups can be used according to the invention to make the branched thermoplastic polymers of the invention, provided that the polymers and their degradation products are biocompatible. The biocompatiblity specifications of such starting monomers is known in the art.

In particular, the monomers used to make the biocompatible thermoplastic branched polymers of the present invention will produce polymers or copolymers that are biocompatible and biodegradable. Examples of biocompatible, biodegradable polymers suitable for use as the biocompatible thermoplastic branched polymers of the present invention include polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), and copolymers, terpolymers, or combinations or mixtures of the above materials.

The polymer composition of the invention can also include polymer blends of the polymers of the present invention with other biocompatible polymers, so long as they do not interfere undesirably with the biodegradable characteristics of the composition. Blends of the polymer of the invention with such other polymers may offer even greater flexibility in designing the precise release profile desired for targeted drug delivery or the precise rate of biodegradability desired for structural implants such as for orthopedic applications.

The preferred biocompatible thermoplastic branched polymers or copolymers of the present invention are those which have a lower degree of crystallization and are more hydrophobic. These polymers and copolymers are more soluble in the biocompatible organic solvents than highly crystalline polymers such as polyglycolide or chitin, which have a high degree of hydrogen-bonding. Preferred materials with the desired solubility parameters are branched polylactides, polycaprolactones, and copolymers of these with glycolide in, which there are more amorphous regions to enhance solubility. Generally, the biocompatible, biodegradable branched thermoplastic polymer is substantially soluble in the organic solvents so that up to 50–60 wt % solids can be made. Preferably, the polymers used according to the invention are essentially completely soluble in the organic solvent so that mixtures up to 85–98 wt % solids can be made. The polymers also are at least substantially insoluble in water so that less than 0.1 g of polymer per mL of water will dissolve or disperse in water. Preferably, the polymers used according to the invention are essentially completely insoluble in water so that less than 0.001 g of polymer per mL of water will dissolve or disperse in water. At this preferred level, the flowable composition with a completely water miscible solventwill almost immediately transform to the solid polymer.

Solvents

Solvents suitable for use in the flowable composition are biocompatible and are at least slightly soluble in aqueous medium, body fluid, or water. The organic solvent preferably is at least moderately soluble, more preferably very soluble, and most preferably soluble at all concentrations in aqueous medium, body fluid, or water. A solvent that is at least slightly soluble in aqueous or body fluid will allow water to permeate into the polymer solution over a period of time ranging from seconds to weeks and cause it to coagulate or solidify. The slightly soluble solvents will slowly diffuse from the flowable composition and typically will enable the transformation over a period of days to weeks, e.g. about a day to several weeks. The moderately soluble to very soluble solvents will diffuse from the flowable composition over a period of minutes to days so that the transformation will occur rapidly but with sufficient leisure to allow its manipulation as a pliable implant after its placement. The highly soluble solvents will diffuse from the flowable composition over a period of seconds to hours so that the transformation will occur almost immediately. The organic solvent preferably is a polar aprotic or polar protic organic solvent. Preferably, the organic solvent has a molecular weight in the range of about 30 to about 1000.

Although it is not meant as a limitation of the invention, it is believed that the transition of the flowable composition to a solid is the result of the dissipation of the organic solvent from the flowable composition into the surrounding aqueous medium or body fluid and the infusion of water from the surrounding aqueous medium or body fluid into the organic solvent within the flowable composition. It is believed that during this transition, the thermoplastic polymer and organic solvent within the flowable composition partition into regions rich and poor in polymer. The regions poor in polymer become infused with water and yield the porous nature of the resulting solid structure.

Examples of biocompatible organic solvents that may be used to form the flowable compositions of the present invention include aliphatic, aryl, and arylalkyl linear, cyclic and branched organic compounds that are liquid or at least flowable at ambient and physiological temperature and contain such functional groups as alcohols, ketones, ethers, amides, esters, carbonates, sulfoxides, sulfones, and any other functional group that is compatible with living tissue.

Preferred biocompatible organic solvents that are at least slightly soluble in aqueous or body fluid include N-methyl-2-pyrrolidone, 2-pyrrolidone; C1 to C15 alcohols, diols, triols and tetraols such as ethanol, glycerine, propylene glycol, butanol; C3 to C15 alkyl ketones such as acetone, diethyl ketone and methyl ethyl ketone; C3 to C15 esters such as methyl acetate, ethyl acetate, ethyl lactate; C1 to C15 amides such as dimethylformamide, dimethylacetamide and caprolactam; C3 to C20 ethers such as tetrahydrofuran, or solketal; tweens, triacetin, propylene carbonate, decylmethylsulfoxide, dimethyl sulfoxide, oleic acid, and 1-dodecylazacycloheptan-2-one. Other preferred solvents are benzyl alcohol, benyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone, 2-pyrrolidone, dimethyl sulfoxide, triacetin, and propylene carbonate because of their solvating ability and their compatibility.

The solubility of the branched biodegradable thermoplastic polymers in the various solvents will differ depending upon their crystallinity, their hydrophilicity, hydrogen-bonding, and molecular weight. Lower molecular-weight polymers will normally dissolve more readily in the solvents than high-molecular-weight polymers. As a result, the concentration of a polymer dissolved in the various solvents will differ depending upon type of polymer and its molecular weight. Moreover, the higher molecular-weight polymers will tend to give higher solution viscosities than the low-molecular-weight materials.

Generally, the concentration of the polymer in the organic solvent according to the invention will range from about 0.01 g per ml of solvent to a saturated concentration. Typically, the saturated concentration will be in the range of 80 to 95 wt % solids or 4 to almost 5 gm per ml of solvent assuming that the solvent weighs approximately 1 gm per ml.

For polymers that tend to coagulate slowly, a solvent mixture can be used to increase the coagulation rate. In essence, one liquid component of the solvent mixture is a good solvent for the polymer, and the other liquid component of the solvent mixture is a poorer solvent or a non-solvent. The two liquids are mixed at a ratio such that the polymer is still soluble but precipitates with the slightest increase in the amount of non-solvent, such as water in a physiological environment. By necessity, the solvent system must be miscible with both the polymer and water. An example of such a binary solvent system is the use of N-methyl pyrrolidone and ethanol. The addition of ethanol to the NMP/polymer solution increases its coagulation rate.

Bioactive Agents

The terms "drug," "medicament," or "bioactive agent" (i.e., biologically active agent) as used herein include without limitation physiologically or pharmacologically active substances that act locally or systemically in the body. A biologically active agent is a substance used for the treatment, prevention, diagnosis, cure or mitigation of disease or illness, a substance which affects the structure or function of the body, or pro-drugs, which become biologically active or more active after they have been placed in a predetermined physiological environment. biologically, physiologically, or pharmacologically active substances that act locally or systemically in the human or animal body. Various forms of the medicaments or biologically active materials can be used which are capable of being released from the solid matrix into adjacent tissues or fluids. The medicaments are at least very slightly water soluble, preferably moderately water soluble, and are diffusible through the polymeric composition. They can be acidic, basic, or amphoteric salts. They can be nonionic molecules, polar molecules, or molecular complexes capable of hydrogen bonding. The biologically-active agent may be included in the compositions in the form of, for example, an uncharged molecule, a molecular complex, a salt, an ether, an ester, an amide, polymer drug conjugate, or other form to provide the effective biological or physiological activity. When the bioactive agent and flowable composition are combined, an embodiment of the pharmaceutical composition is provided.

Bioactive agents contemplated for use with the flowable composition of the present include anabolic agents, antacids, anti-asthmatic agents, anti-cholesterolemic and anti-lipid agents, anti-coagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, anti-pyretic and analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

More particularly, the biologically active agents preferred for use with the flowable composition of the present invention include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines. Representative drugs or bioactive materials that can be used in the polymer system or solid matrix of the present invention include, but are not limited to, peptide drugs, protein drugs, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, β-adrenergic blocking agents, nutritional agents, and the benzophenanthridine alkaloids. The agent may further be a substance capable of acting as a stimulant, sedative, hypnotic, analgesic, anticonvulsant, and the like.

The pharmaceutical composition can contain a large number of biologically active agents either singly or in combination. The biologically active agents can be in a controlled release component, which is dissolved, dispersed or entrained in the adjunctive polymer system. The controlled release component can include microstructures, macrostructures, conjugates, complexers, low water-solubility salts and the like. Microstructures include nanoparticles, cyclodextrins, microcapsules, micelles, lipsomes and the like. Macrostructures include fibers, beads and the like. Controlled release compositions are disclosed in U.S. Pat. No. 5,702,716, the disclosure of which is incorporated herein by reference.

Examples of these biologically-active agents include, but are not limited to:

Anti-inflammatory agents such as hydrocortisone, prednisone, fludrotisone, triamcinolone, dexamethasone, betamethasone, and the like.

Anti-bacterial agents such as penicillins, cephalosporins, vancomycin, bacitracin, polymycins, tetracyclines, chloramphenicol, erythromycin, streptomycin, quinolone, and the like.

Antifungal agents such as nystatin, gentamicin, miconazole, tolnaftate, undecyclic acid and its salts, and the like.

Analgesic agents such as salicylic acid, salicylate esters and salts, acetaminophen, ibuprofen, morphine, phenylbutazone, indomethacin, sulindac, tolmetin, zomepirac, and the like.

Local anesthetics such as cocaine, benzocaine, novocaine, lidocaine, and the like.

The bioactive material may also be a substance, or metabolic precursor thereof, which is capable of promoting growth and survival of cells and tissues, or augmenting the activity of functioning cells, as for example, blood cells, neurons, muscle, bone marrow, bone cells and tissues, and the like. For example, the bioactive material may be a nerve growth promoting substance, as for example, a ganglioside, phosphatidylserine, a nerve growth factor, brain-derived neurotrophic factor. The bioactive material may also be a growth factor for soft or fibrous connective tissue as, for example, a fibroblast growth factor, an epidermal growth factor, an endothelial cell growth factor, a platelet derived growth factor, an insulin-like growth factor, a periodontal ligament cell growth factor, cementum attachment extracts, and fibronectin.

To promote bone growth, the biologically active material may be an osteoinductive or osteoconductive substance. Suitable bone growth promoting agents include, for example, osteoinductive factor (OIF), bone morphogenetic protein (BMP) or protein derived therefrom, demineralized bone matrix, and releasing factors thereof. Further, the agent may be a bone growth promoting substance such as hydroxyapatite, tricalcium phosphate, a di- or polyphosphonic acid, an anti-estrogen, a sodium fluoride preparation, a substance having a phosphate to calcium ratio similar to natural bone, and the like. A bone growth promoting substance may be in the form, as for example, of bone chips, bone crystals or mineral fractions of bone and/or teeth, a synthetic hydroxyapatite, or other suitable form. The agent may further be capable of treating metabolic bone disorders such as abnormal calcium and phosphate metabolism by, for example, inhibiting bone resorption, promoting bone mineralization, or inhibiting calcification. The active agent may also be used to promote the growth and survival of blood cells, as for example, a colony stimulating factor, and erythropoietin.

Upon formation of the solid matrix from the pharmaceutical composition, the biologically active agent becomes incorporated into the polymer matrix. The bioactive agent will be released from the matrix into the adjacent tissues or fluids by diffusion, migration, dissolution, and by polymer erosion and degradation mechanisms. Manipulation of these mechanisms also can influence the release of the bioactive agent into the surroundings at a controlled rate. For example, the polymer matrix can be formulated to degrade after an effective and/or substantial amount of the bioactive agent is released from the matrix. Release of a agent having a low solubility in water, as for example a peptide or protein, typically requires the degradation of a substantial part of the polymer matrix to expose the agent directly to the surrounding tissue fluids. Thus, the release of the biologically active agent from the matrix can be varied by, for example, the solubility of the bioactive agent in water, the distribution of the bioactive agent within the matrix, or the size, shape, porosity, solubility and biodegradability of the polymer matrix, among other factors. The release of the biologically active agent can facilitate pore formation. The release of the biologically active agent from the matrix is controlled relative to its intrinsic rate by varying the polymer composition, molecular weight, and/or polymer concentration, and by adding a rate modifying agent to provide a desired duration and rate of release, as described above.

The pharmaceutical composition is formulated to provide a solid matrix containing the bioactive agent in an amount effective to provide a desired biological, physiological and/ or therapeutic effect. The "effective amount" of a biologically active agent incorporated into the pharmaceutical composition of the invention depends on a variety of factors, such as the desired release profile, the concentration of bioactive agent required for a desired biological effect, and the period of time over which the bioactive agent needs to be released for desired treatment. Ultimately, this amount is determined by the patient's physician who will apply his experience and wisdom in prescribing the appropriate kind and amount of bioactive agent to provide therapy for the patient. There is generally no critical upper limit on the amount of bioactive agent incorporated into the polymer solution. The only limitation is a physical limitation for advantageous application, i.e., the bioactive agent should not be present in such a high concentration that the solution or dispersion viscosity is too high for use. The lower limit of bioactive agent incorporated into the polymer system typically depends only on the activity of the bioactive agent and the period of time desired for treatment.

To those skilled in the art, any biologically active agent that can be released in an aqueous environment can be utilized in the described pharmaceutical composition. Also, various forms of the biologically active agents may be used. These include without limitation forms such as uncharged molecules, molecular complexes, salts, ethers, esters, amides, etc., which are biologically activated when injected into the body.

Bioactive agents can be combined with the flowable composition to provide a pharmaceutical composition for drug delivery. In its simplest form, the pharmaceutical composition is a dispersion or solution of the bioactive agent in a matrix of the biocompatible, biodegradable, branched thermoplastic polymer.

To prepare such a pharmaceutical composition, a bioactive agent is added to the flowable composition of the present invention prior to its use. Then the pharmaceutical composition is administered or otherwise processed to cause its transformation in vivo or ex vivo to the desired implant, implantable article, medical device and the like.

In some cases, the bioactive agent will be soluble in the solvent, and a homogenous solution of flowable composition and bioactive agent will be available for transformation processing. In other cases, the bioactive agent will not be soluble in the solvent, and a suspension or dispersion of the bioactive agent in the flowable composition will result. This suspension or dispersion can also be processed to transform it into the desired implant, implantable article and the like. In either case, the solvent will dissipate and the polymer will solidify and incorporate the bioactive agent within the solid matrix. The release of bioactive agent from these solid implants will follow the same general rules for release of a bioactive agent from a monolithic polymeric device. The release of bioactive agent can be affected by the size and shape of the implant, the loading of bioactive agent within the implant, the permeability factors involving the bioactive agent and the particular polymer, and the degradation of the polymer. Depending upon the bioactive agent selected for delivery, the above parameters can be adjusted by one skilled in the art of drug delivery to give the desired rate and duration of release.

Pursuant to the parameters and conditions of the invention, the release of the bioactive agent can be controlled. In particular, the rate and extent of release of the bioactive agent from an implant, implantable article, device and the like according to the invention can be controlled by variation of the polymer type and molecular weight, use of a rate modifying agent, use of plasticizers and leachable agents and the concentrations and kinds of thermoplastic polymer and bioactive agent.

Rate modifying agents, plasticizers and leachable agents can be included to manage the rate of release of bioactive agent and the pliability of the matrix. The rate modifying agent can increase or retard the rate of release depending upon the nature of the rate modifying agent incorporated into the solid matrix according to the invention. Known plasticizers as well as organic compounds that are suitable for secondary pseudobonding in polymer systems are acceptable as rate modifying agents and also as pliability modifiers and leaching agents. Generally these agents are esters of mono, di and tricarboxylic acids, diols and polyols, polyethers, non-ionic surfactants, fatty acids, fatty acid esters, oils such as vegetable oils, and the like. The concentrations of such agents within the solid matrix can range in amount up to 60 wt % relative to the total weight of the matrix, preferably up to 30 wt % and more preferably up to 15 wt %. Generally, these rate modifying agents, leaching agents, plasticizers and pliability modifiers and their application are described in U.S. Pat. Nos. 5,702,716 and 5,447,725, the disclosures of which are incorporated herein by reference with the proviso that the polymers to be used are the biocompatible, biodegradable, branched thermoplastic polymers of the present invention.

Moldable Implant Precursor

The flowable composition can be formed into a moldable implant precursor by its contact with an aqueous medium such as water or saline, or contact with a body fluid such as blood serum, lymph, and the like pursuant to the techniques disclosed in U.S. Pat. No. 5,487,897, the disclosure of which is incorporated herein by reference with the specification that the thermoplastic polymer of the '897 patent is a biocompatible, biodegradable, branched thermoplastic polymer as described herein.

Briefly, the technique disclosed by the '897 patent converts the flowable composition with or without bioactive agent into a two-part structure comprising an outer sac with a flowable content. The technique applies a limited amount of aqueous medium and the like to a quantity of the pharmaceutical system so that only the outer surface of the system is converted to solid, thus forming the sac with a flowable content inside. The flowable content of the implant precursor may range in consistency from watery to viscous. The outer sac may range in consistency from gelatinous to an impressionable, moldable and waxen-like. The resulting device, or implant precursor, may then be applied to an implant site. Upon implantation, the solvent from the implant precursor diffuses into the surrounding tissue fluids to form an implant having a solid polymer matrix. Preferably, the implant precursor solidifies in situ to a solid matrix within about 0.5–4 hours after implantation, preferably within about 1–3 hours, preferably within about 2 hours. Thus, when placed into an implant site in a body, the implant precursor eventually coagulates to a solid, microporous matrix structure.

Porous Structure

The porous structure of the solid matrices, e.g., in situ formed implants, implants, implantable articles, biodegradable articles and devices of the invention, is influenced by nature of the organic solvent and branched thermoplastic polymer, by their solubility in water, aqueous medium or body fluid (which may differ for each medium) and by the presence of an additional pore forming moiety. The porous structure is believed to be formed by several mechanisms and their combinations. The dissipation, disbursement or diffusion of the solvent out of the solidifying flowable composition into the adjacent fluids may generate pores, including pore channels, within the polymer matrix. The infusion of aqueous medium, water or body fluid into the flowable composition also occurs and is in part also responsible for creation of pores. Generally, it is believed that the porous structure is formed during the transformation of the flowable composition to a solid implant, article and the like. During this process, it is believed, as explained above, that the organic solvent and thermoplastic polymer partition within the flowable composition into regions that are rich and poor in thermoplastic polymer. The partition is believed to occur as a result of the dynamic interaction of aqueous infusion and solvent dissipation. The infusion involves movement of aqueous medium, water or body fluid into the flowable composition and the dissipation involves movement of the organic solvent into the medium surrounding the flowable composition. The regions of the flowable composition that are poor in thermoplastic polymer become infused with a mixture of organic solvent and water, aqueous medium or body fluid. These regions are believed to eventually become the porous network of the solid implant, article and the like.

Typically, the macroscopic structure of the solid matrix involves a core and a skin. Typically, the core and skin are microporous but the skin pores are of smaller size than those of the core unless a separate pore forming agent is used as discussed below. Preferably, the outer skin portion of the solid matrix has pores with diameters significantly smaller in size than these pores in the inner core portion. The pores of the core are preferably substantially uniform and the skin is typically functionally non-porous compared to the porous nature of the core. The size of the pores of the solid implant, article, device and the like are in the range of about 4–1000 microns, preferably the size of pores of the skin layer are about 1–500 microns. The porosity of such matrices is described by U.S. Pat. No. 5,324,519, the disclosure of which is incorporated herein by reference.

The solid microporous implant, article, device and the like will have a porosity in the range of about 5–95% as measured by the percent solid of the volume of the solid. The development of the degree of porosity will be governed at least in part by the degree of water solubility of the organic solvent and branched thermoplastic polymer. If the water solubility of the organic solvent is high and that of the polymer is extremely low or non-existent, a substantial degree of porosity will be developed, typically on the order of 30 to 95%. If the organic solvent has a low water solubility and the polymer has a low to non-existent water solubility, a low degree of porosity will be developed, typically on the order of 5 to 40%. It is believed that the degree of porosity is in part controlled by the polymer-solvent partition when the flowable composition contacts an aqueous medium and the like. The control of the degree of porosity is beneficial for generation of differing kinds of biodegradable articles, implants and devices according to the invention. For example, if strength is a requirement for the article, implant or device and the like, it may be beneficial to have a low degree of porosity. Sutures and clips are such examples.

Pore Forming Additive

Additives can be used to advantage in further controlling the pore size in the solid matrix, which influences the structure of the matrix and the release rate of a bioactive agent or the diffusion rate of body fluids. For example, if the flowable composition is too impervious to aqueous medium, water or tissue ingrowth, a pore-forming agent can be added to generate additional pores in the matrix. Any biocompatible water-soluble material can be used as the pore-forming additive. These additives can be either soluble in the flowable composition or simply dispersed within it. They are capable of dissolving, diffusing or dispersing out of both the coagulating polymer matrix whereupon pores and microporous channels are generated. The amount of pore-forming additive (and size of dispersed particles of such pore-forming agent, if appropriate) within the flowable composition will directly affect the size and number of the pores in the polymer matrix.

Pore-forming additives include any pharmaceutically acceptable organic or inorganic substance that is substantially miscible in water and body fluids and will dissipate from the forming and formed matrix into aqueous medium or body fluids or water-immiscible substances that rapidly degrade to water soluble substances. It is further preferred that the pore-forming additive is miscible or dispersible in the organic solvent to form a uniform mixture. Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone. The size and extent of the pores can be varied over a wide range by changing the molecular weight and percentage of pore-forming additive incorporated into the flowable composition.

As indicated, upon contact with body fluid, the solvent and optional pore-forming additive dissipate into surrounding tissue fluids. This causes the formation of microporous channels within the coagulating polymer matrix. Optionally, the pore-forming additive may dissipate from the matrix into the surrounding tissue fluids at a rate slower than that of the solvent, or be released from the matrix over time by biodegradation or bioerosion of the matrix. Preferably, the pore-forming additive dissipates from the coagulating implant matrix within a short time following implantation such that a matrix is formed with a porosity and pore structure effective to perform the particular purpose of the implant, as for example, a barrier system for a tissue regeneration site, a matrix for timed-release of a drug or medicament, and the like.

Porosity of the solid polymer matrix may be varied by the concentration of water-soluble or water-miscible ingredients, such as the solvent and/or pore-forming agent, in the polymer composition. For example, a high concentration of water-soluble substances in the thermoplastic composition may produce a polymer matrix having a high degree of porosity. The concentration of the pore-forming agent relative to polymer in the composition may be varied to achieve different degrees of pore-formation, or porosity, in the matrix. Generally, the polymer composition will include about 0.01–1 gram of pore-forming agent per gram polymer.

The size or diameter of the pores formed in the matrix of the solid implant may be modified according to the size and/or distribution of the pore-forming agent within the polymer matrix. For example, pore-forming agents that are relatively insoluble in the polymer mixture may be selectively included in the polymer composition according to particle size in order to generate pores having a diameter that corresponds to the size of the pore-forming agent. Pore-forming agents that are soluble in the polymer mixture may be used to vary the pore size and porosity of the implant matrix by the pattern of distribution and/or aggregation of the pore-forming agent within the polymer mixture and coagulating and solid polymer matrix.

Where the implant is used to promote guided tissue regeneration, it is preferred that the diameter of the pores in the matrix are effective to deter growth of epithelial cells and enhance growth of connective tissue cells into the polymer matrix of the implant. It is further preferred that the size of the pores and porosity of the matrix of the implant facilitate diffusion of nutrients and other growth-promoting substances such as growth factors, to cells which have grown into the matrix. Preferably, the degree of porosity of the matrix provides an implant that is capable of substantially maintaining structural integrity for the desired period of time without breakage or fracturing during use.

To provide an effective implant for bone cell regrowth and tissue regeneration, it is preferred that the diameter of the pores of the implant is about 3–500 microns, more preferably about 3–200 microns, more preferably about 75–150 microns. It is further preferred that the matrix has a porosity of about 5–95%, preferably about 25–85%, in order to provide optimum cell and tissue ingrowth into the matrix and optimum structural integrity.

Pore diameter and distribution within the polymer matrix of the solid implant may be measured, as for example, according to scanning electron microscopy methods by examination of cross-sections of the polymer matrix. Porosity of the polymer matrix may be measured according to suitable methods known in the art, as for example, mercury intrusion porosimetry, specific gravity or density comparisons, calculation from scanning electron microscopy photographs, and the like. Additionally, porosity may be calculated according to the proportion or percent of water-soluble material included in the polymer composition. For example, a polymer composition which contains about 30% polymer and about 70% solvent and/or other water-soluble components will generate an implant having a polymer matrix of about 70% porosity.

In a particularly preferred embodiment, an article is used for implantation, injection, or otherwise placed totally or partially within the body, the article comprising the biodegradable polymer composition of the invention. The biologically active substance of the composition and the polymer of the invention may form a homogeneous matrix, or the biologically active substance may be encapsulated in some way within the polymer. For example, the biologically active substance may be first encapsulated in a microsphere and then combined with the polymer in such a way that at least a portion of the microsphere structure is maintained. Alternatively, the biologically active substance may be sufficiently immiscible in the polymer of the invention that it is dispersed as small droplets, rather than being dissolved, in the polymer. Either form is acceptable, but it is preferred that, regardless of the homogeneity of the composition, the release rate of the biologically active substance in vivo remain controlled, at least partially as a function of hydrolysis of the ester bond of the polymer upon biodegradation.

In a preferred embodiment, the article of the invention is designed for implantation or injection into the body of a mammal. It is particularly important that such an article result in minimal tissue irritation when implanted or injected into vasculated tissue. As a structural medical device, the polymer compositions of the invention provide a physical form having specific chemical, physical, and mechanical properties sufficient for the application and a composition that degrades in vivo into non-toxic residues. Typical structural medical articles include such implants as orthopedic fixation devices, ventricular shunts, laminates for degradable fabric, drug-carriers, biosorbable sutures, burn dressings, coatings to be placed on other implant devices, and the like.

In orthopedic articles, the composition of the invention may be useful for repairing bone and connective tissue injuries. For example, a biodegradable porous material can be loaded with bone morphogenetic proteins to form a bone graft useful for even large segmental defects. In vascular graft applications, a biodegradable material in the form of woven fabric can be used to promote tissue ingrowth. The polymer composition of the invention may be used as a temporary barrier for preventing tissue adhesion, e.g., following abdominal surgery.

On the other hand, in nerve regeneration articles, the presence of a biodegradable supporting matrix can be used to facilitate cell adhesion and proliferation. When the polymer composition is fabricated as a tube for nerve generation, for example, the tubular article can also serve as a geometric guide for axonal elongation in the direction of functional recovery.

As a drug delivery device, the polymer compositions of the invention provide a polymeric matrix capable of sequestering a biologically active substance and provide predictable, controlled delivery of the substance. The polymeric matrix then degrades to non-toxic residues.

In all cases, the solid implant formed within the injectable polymer solution will slowly biodegrade within the body and allow natural tissue to grow and replace the impact as it disappears. Thus, when the material is injected into a soft-tissue defect, it will fill that defect and provide a scaffold for natural collagen tissue to grow. This collagen tissue will gradually replace the biodegradable polymer. With hard tissue such as bone, the biodegradable polymer will support the growth of new bone cells, which will also gradually replace the degrading polymer. For drug-compositions, the solid implant formed from the injectable system will release the drug contained within its matrix at a controlled rate until the drug is depleted. With certain drugs, the polymer will degrade after the drug has been completely released. With other drugs such as peptides or proteins, the drug will be completely released only after the polymer has degraded to a point where the non-diffusing drug has been exposed to the body fluids.

Solid Biodegradable Articles

Biodegradable medical implants, microcapsules, microparticles, medical devices and drug delivery products can be prepared by the transformation process using water or an aqueous medium or body fluid to cause solidification. Generally, these products are ex vivo solid matrices. If the ex vivo solid matrix is to have a particular shape, such as a stent or medical device, it can be obtained by transforming the flowable composition in a suitable mold following the moldable implant precursor technique described above. After the precursor has been formed, it can be contacted with additional aqueous medium to complete the transformation. Alternatively, the flowable composition can be placed in a closed mold that is permeable to aqueous medium and the mold with composition can be contacted with aqueous medium such as be submerging in an aqueous bath. Preferably, the flowable composition in this instance will have a moderate to high viscosity.

Microcapsules and microparticles can be formed by techniques known in the art. Briefly, the microcapsule preparation involves formation of an emulsion of bioactive agent-carrier micelles in the flowable composition where the carrier is a nonsolvent for the biocompatible, biodegradable, branched thermoplastic polymer of the invention. The micelles are filtered and then suspended in an aqueous medium. The coating of flowable composition on the surfaces of the micelles then solidifies to form the porous microcapsules. Microparticles are formed in a similar process. A mixture of flowable composition and bioactive agent is added dropwise by spraying, dripping, aerosolizing or by other similar techniques to a nonsolvent for the flowable composition. The size and shape of the droplets is controlled to produce the desired shape and size of the porous microparticles. Sheets, membranes and films can be produced by casting the flowable composition onto a suitable nonsolvent and allowing the transformation to take place. Similarly, the viscosity of the flowable composition can be adjusted so that when sprayed or aerosolized, strings rather than droplets are formed. These strings can be cast upon a nonsolvent for the flowable composition such that a filamentous scaffold or membrane is produced. Also, suture material or other similar material can be formed by extrusion of the flowable composition into a non-solvent bath. The extrusion orifice will control the size and shape of the extruded product. The techniques for formation of these ex vivo solid matrices are described in U.S. Pat. Nos. 4,652,441; 4,917,893; 4,954,298; 5,061,492; 5,330,767; 5,476,663; 5,575,987; 5,480,656; 5,643,607; 5,631,020; 5,631,021; 5,651,990, the disclosures of which are incorporated herein by reference with the proviso that the polymers used are the biocompatible, biodegradable, branched thermoplastic polymers of the invention.

These ex vivo solid matrices can be used according to their known functions. For example, fasteners such as sutures and staples can be used according to known techniques in the art. The implants and other solid articles are can be inserted in a body using techniques known to the art such as through an incision or by trocar.

EXAMPLES

The present invention is more particularly described in the following examples which are intended for illustration purposes only, since numerous modifications and variations will be apparent to those skilled in the art.

Example 1

Biodegradable Polymer Synthesis

A 360 ml teflon vessel was charged with D,L lactide (275 g), polyol (0.4–1.1 w/w %), and stannous octoate (0.045 w/w %). The mixture was heated at 145° C. for 20 hours. The resulting polyester was removed from the reaction vessel and dissolved in anhydrous dichloromethane and purified by precipitation in anhydrous methanol. The polymers were dried under vacuum at ambient temperature to remove most of the residual solvent. The resulting hard, solid masses were cooled in liquid nitrogen and cut into small pieces. The small pieces were ground in a Wiley mill to a coarse dust sufficient to pass through a 6 mm screen. The resulting polymer was dried under vacuum at ambient temperature prior to final packaging.

Example 2

Biodegradable Polymer Characterization

Weight average molecular weights from light scattering were determined using a system incorporating a Waters 510 pump, two Polymer Labs "Mixed C" columns in series, a Shimadzu CTO-10-A column oven, a Waters 410 differential refractometer, and a Minidawn® multiangle light scattering detector (Wyatt Technologies). Data were obtained and analyzed on a PC using Astra® software (Wyatt Technologies). Data are reported in Daltons. Weight average molecular weights and number average molecular weights from conventional calibration were obtained using the system described above through the Waters 410 differential refractometer using a Polymer Labs data capture unit and Caliber® software. A calibration curve was obtained using Polymer Laboratories Easi-Cal PS-1 polystyrene standards. Data are reported in Daltons. Inherent Viscosities (IV) were obtained using polymer solutions of 0.45 to 0.55 percent weight/volume in a Canon-Fenske viscometer, size 25, at 30° C. Data are reported in dL/g. Brookfield Viscosities (BV) were obtained for polymer solutions of 40 prevent weight/weight solutions in N-methyl-pyrolidone using a Brookfield Digital Viscometer with a SC4-218 spindle at 0.3 rpm and 25 ° C. Data are reported in centipoise. The polymer characterization data is summarized in Table 1. Data indicate that branched polymers derived from at least trifunctional triols have comparable molecular weights to the linear polymers, but substantially lower viscosities, particularly Brookfield Viscosities.

TABLE 1

Polymer Characterization Data
Data for Linear and Branched Poly(DL-lactide)s

| Sample | A107-35 | A107-41 | A107-43 | A107-55 |
|---|---|---|---|---|
| Initiator | Dodecanol | Ethylene Glycol | Trimethylolpropane | Pentaerythritol |
| Molecular Architecture | Linear | Linear | Tribranched | Tetrabranched |
| End Groups | 1 Hydroxyl, 1 Ester | 2 Hydroxyl | 3 Hydroxyl | 4 Hydroxyl |
| Mw (LS) | 17,000 | 18,300 | 17,500 | 16,200 |
| Mw (CC) | 23,100 | 25,800 | 22,400 | 21,600 |
| Mn (CC) | 17,100 | 19,300 | 18,500 | 18,100 |
| IV, dL/g | 0.34 | 0.32 | 0.30 | 0.22 |
| BV, cP | 1880 | 1410 | 890 | 690 |

Example 3

Biodegradable Polymer Degradation Studies

Figure 2:
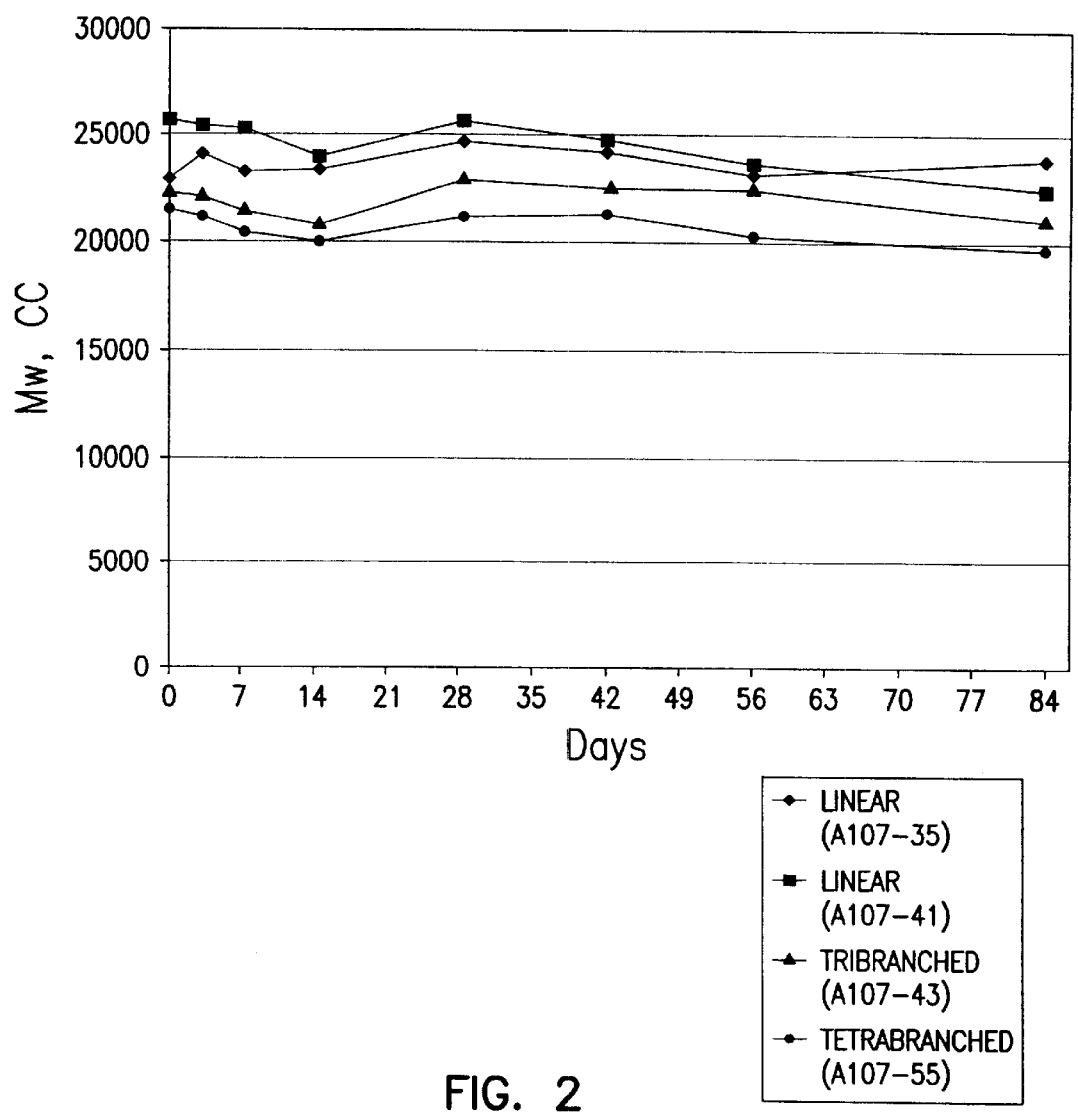
FIG. 2 shows the results of Degradation Study 2.
Figure 3:
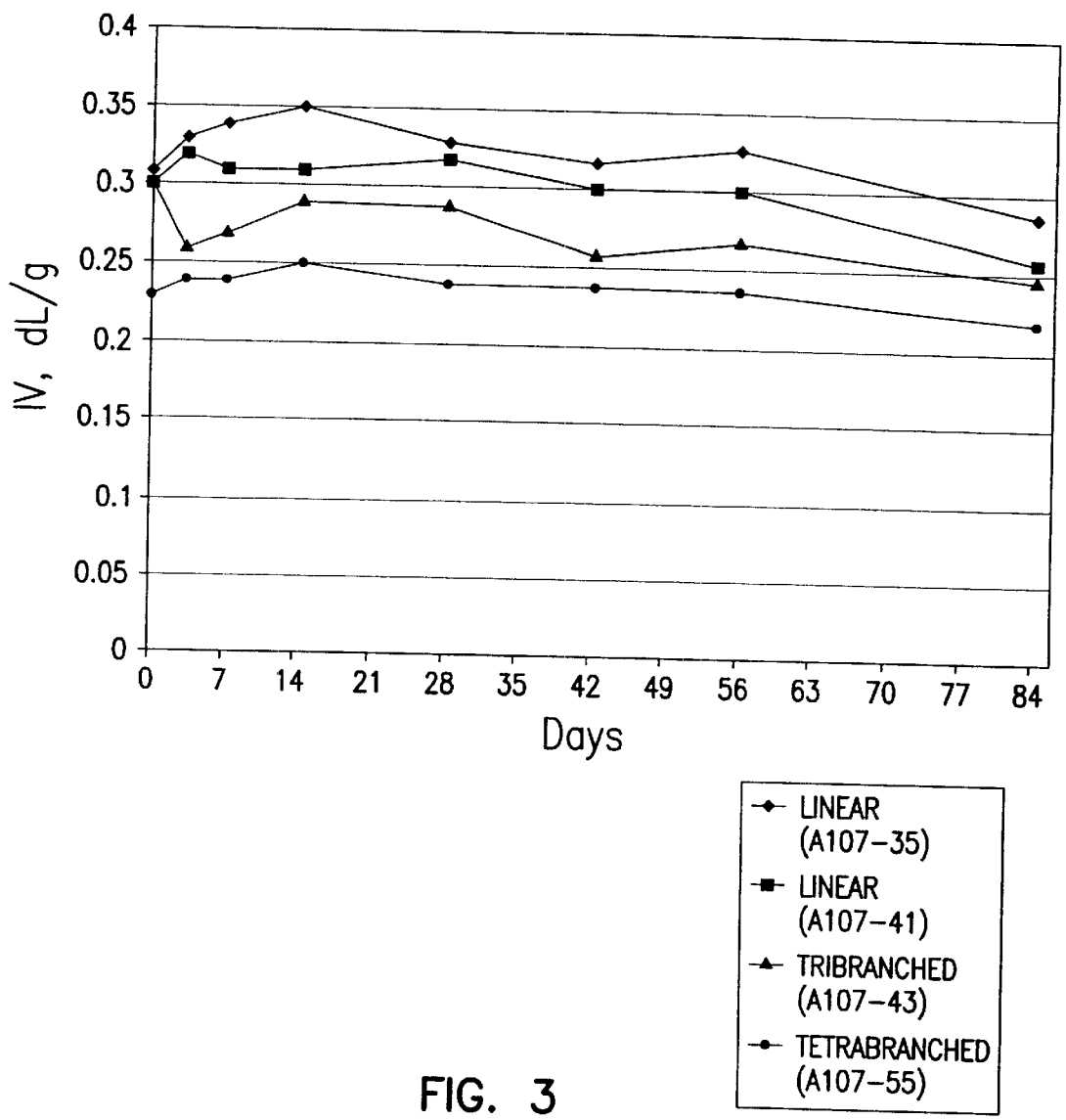
FIG. 3 shows the Inherent Viscosities (IV) of the polymers in Degradation Study 3.

The biodegradable polymers were degraded in duplicate samples and analyzed at seven time points: no exposure; 3 days; 7 days; 14 days; 28 days; 42 days; 56 days; and 84 days. Approximately 0.5 g of biodegradable polymer were shaken in glass jars containing 100 ml of 0.01 M phosphate buffer saline (PBS) with a pH of 7.4 at 37° C. in an environmental shaker. The buffer was changed at 72 hour intervals. At each time point, the samples were isolated and vacuum dried. Each sample was analyzed twice for GPC (LS), GPC (CC), and IV as described in Example 2. The two runs were averaged to construct degradation profiles. The results of the degradation studies are summarized in FIGS. 1–3.

Example 4

Controlled Release Studies

Figure 4:
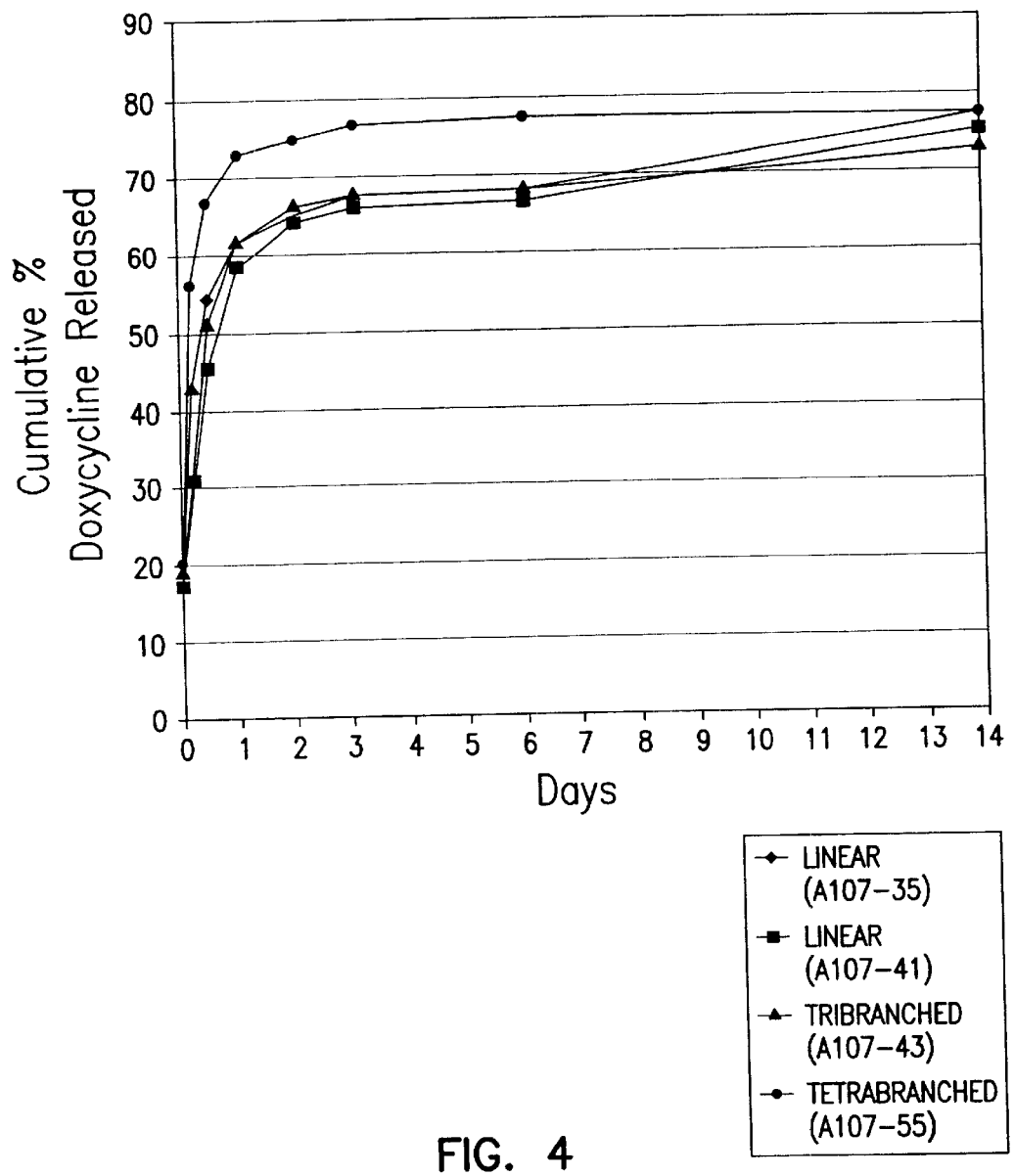
FIG. 4 shows drug release data of the biodegradable polymers loaded with doxycycline hyclate.

The biodegradable polymer of the present invention dissolved in N-methyl pyrollidone was loaded into a 1 ml syringe. Doxycycline hyclate was loaded into another 1 ml syringe to give a drug load of 8.5 percent doxycycline. The syringes were coupled together and mixed for 50 cycles. The syringe was then placed on a scale and tared. The composition containing doxycycline was then dropped into 5 ml phosphate buffer solution at a pH of 7.40 and a temperature of 37° C. The syringe was then placed back on the scale and the implant weight was recorded. This was repeated for each formulation four more times to give an n of five at each time point. The samples were then placed in an environmental shaker at 37° C. with a speed of 150 RPMs. At various time points, the phosphate buffer solution was decanted and the polymer implant was left in the vial. A fresh 5 ml of phosphate buffer solution was added to the precipitated polymer and placed back in the shaker. The phosphate buffer solution that was decanted was then analyzed by UV visibility for doxycycline content. Based upon the implant weight a theoretical amount of doxycycline was calculated. Drug release was then based upon this theoretical amount. Release data are depicted in FIG. 4.

What is claimed is:

1. A pharmaceutical system suitable for forming a biodegradable article for use in a body, the pharmaceutical system comprising: a flowable composition of a biocompatible, biodegradable, branched, thermoplastic polymer that is at least substantially insobule in aqueous medium, water, or body fluid; and a biocompatible organic solvent that is at least slightly soluble in aqueous medium, water, or body fluid;

wherein the polymer is selected from the group consisting of polyamides, polyurethanes, polyureas, copolymers, terpolymers, combinations, and mixtures thereof.

2. A pharmaceutical system according to claim 1 wherein the polymer comprises one or more polyamides.

3. A pharmaceutical system according to claim 1 wherein the polymer comprises one or more polyurethanes.

4. A pharmaceutical system according to claim 1 wherein the polymer comprises one or more polyureas.

5. A pharmaceutical system according to claim 1 wherein the polymer has polymer chains or backbones comprising monomeric unit linking groups that can be hydrolyzed by enzymatic reaction or hydrolysis reaction.

6. A pharmaceutical system according to claim 1 wherein the biocompatible biodegradable branched thermoplastic polymer is formed at least in part from a monomer that has at least three functional groups.

7. A pharmaceutical system according to claim 1 wherein the biocompatible organic solvent is at least moderately soluble in aqueous medium, water or body fluid.

8. A pharmaceutical system according to claim 1 wherein the biocompatible organic solvent has a molecular weight in the range of about 30 to about 500.

9. A pharmaceutical system according to claim 1 wherein the biocompatible organic solvent is a polar aprotic organic solvent or polar protic organic solvent.

10. A pharmaceutical system according to claim 1 wherein the biocompatible organic solvent is a cyclic, branched or linear aliphatic, aryl, or arylalkyl organic compound that is liquid at ambient and physiological temperature and contains at least one functional group selected from the group consisting of alcohols, ketones, ethers, amides, amides, esters, carbonates, sulfoxides, sulfones, and combinations thereof.

11. A pharmaceutical system according to claim 1 wherein the biocompatible organic solvent is selected from the group consisting of N-methyl-2-pyrrolidone, 2-pyrrolidone, C2 to C6 alkanols, propylene glycol, solketal, acetone, methyl acetate, ethyl acetate, ethyl lactate, methyl ethyl ketone, dimethylformamide, dimethyl sulfoxide, dimethyl sulfone, tetrahydrofuran, caprolactam, decylmethylsulfoxide, oleic acid, propylene carbonate, triacetin, N,N-diethyl-m-toluamide, and 1-dodecylazacycloheptan-2-one.

12. A pharmaceutical system according to claim 1 further comprising a biologically active agent.

13. A pharmaceutical system according to claim 12, wherein the biologically active agent is a single entity or a combination of entities having at least slight water solubility.

14. A pharmaceutical system according to claim 12, wherein the biologically active agent is a substance used for the treatment, prevention, diagnosis, cure or mitigation of disease or illness, a substance which affects the structure or function of the body, or pro-drugs, which become biologically active or more active after they have been placed in a predetermined physiological environment.

15. A pharmaceutical system according to claim 12, wherein the biologically active agent is selected from the group consisting of anabolic agents, antacids, anti-asthmatic agents, anti-cholesterolemic and anti-lipid agents, anticoagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, anti-pyretic and analgesic agents, antispasmodic agents, anti-thrombotic agents, anti-tussive agents, anti-uricemic agents, anti-anginal agents, antihistamines, anti-tussives, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and antithyroid agents, tissue growth agents, uterine relaxants, vitamins, and antigenic materials.

16. A pharmaceutical system according to claim 12, wherein the biologically active agent is selected from the group consisting of androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

17. A pharmaceutical system according to claim 1 wherein the percent solids of the branched thermoplastic polymer in the flowable composition is in the range of about 0.01 wt % to about 95 wt % relative to the total weight of the flowable composition.

18. A pharmaceutical system according to claim 17 wherein the percent solids is in the range of about 2 wt % to about 80 wt %.

19. A pharmaceutical system according to claim 17 wherein the percent solids is in the range of about 5 wt % to about 70wt %.

20. A pharmaceutical system according to claim 17 wherein the percent solids is in the range of about 30 wt % to about 80wt %.

21. A pharmaceutical system according to claim 1 that is capable of forming a microporous matrix upon its contact with aqueous medium, water or body fluid, wherein the matrix is a core surrounded by a skin, the core containing pores of diameters from about 1 to 1000 microns, and the skin containing pores of smaller diameters than those of the core pores.

22. A pharmaceutical system according to claim 21, wherein the skin pores are of a size such that the skin is functionally non-porous in comparison with the pores.

23. A pharmaceutical system according to claim 1 wherein the flowable composition is convertible to fasteners, microcapsules, microparticles, implants, or coatings on implants.

24. A biocompatible article which is produced by contacting aqueous medium, water or body fluid and a flowable composition of a biocompatible, biodegradable, branched, thermoplastic polymer that is at least substantially insoluble in aqueous medium, water or body fluid, and a biocompatible organic solvent that is at least slightly soluble in aqueous medium, water or body fluid;

wherein the polymer is selected from the group consisting of polyamides, polyurethanes, polyureas, copolymers, terpolymers, combinations, and mixtures thereof.

25. An article according to claim 24 which is in the form of a absorbable fasteners, microcapsules, microparticles, implants, or a coating on an implant.

26. An article according to claim 24 which is produced ex vivo.

27. An article according to claim 24 which is produced in situ.

28. A method for the controlled release of a biologically active agent comprising placing in a body a pharmaceutical system according to claim 12 and allowing the pharmaceutical system to form an in situ implant containing the biologically active agent.

29. A method according to claim 28 wherein the pharmaceutical system is adaptable for implantation or injection into a body.

30. A method according to claim 28, which is convertible to implants for controlled drug release suitable for providing a biological, therapeutic, or physiological effect in a living organism.

31. A method according to claim 28 which is convertible to microcapsules for controlled drug release suitable for providing a biological, therapeutic, or physiological effect in a living organism.

32. A method according to claim 28 which is convertible to absorbable fasteners suitable for providing a biological, therapeutic, or physiological effect in a living organism.

33. A method according to claim 28 which is convertible to a material for treating bone injuries suitable for providing a biological, therapeutic, or physiological effect in a living organism.

34. A method according to claim 28 which is convertible to a coating on an implant device suitable for providing a biological, therapeutic, or physiological effect in a living organism.

* * * * *

UNITED STATES PATENT AND TRADEMARK OFFICE
CERTIFICATE OF CORRECTION

PATENT NO. : 6,528,080 B2
DATED : March 4, 2003
INVENTOR(S) : Dunn et al.

It is certified that error appears in the above-identified patent and that said Letters Patent is hereby corrected as shown below:

<u>Title page,</u>
Item [73], Assignee, after "Atrix Laboratories, Inc., Fort Collins, CO (US)" insert
-- Absorbable Polymer Technologies, Inc., Pelham, AL (US) --.

Signed and Sealed this

Sixteenth Day of September, 2003

JAMES E. ROGAN
*Director of the United States Patent and Trademark Office*